United States Patent
Bulkes

(10) Patent No.: US 7,310,556 B2
(45) Date of Patent: Dec. 18, 2007

(54) IMPLANTABLE MEDICAL STIMULATION APPARATUS WITH INTRA-CONDUCTOR CAPACITIVE ENERGY STORAGE

(75) Inventor: Cherik Bulkes, Sussex, WI (US)

(73) Assignee: Kenergy, Inc., Mequon, WI (US)

( * ) Notice: Subject to any disclaimer, the term of this patent is extended or adjusted under 35 U.S.C. 154(b) by 307 days.

(21) Appl. No.: 11/089,476

(22) Filed: Mar. 24, 2005

(65) Prior Publication Data

US 2006/0217767 A1   Sep. 28, 2006

(51) Int. Cl.
*A61N 1/375*   (2006.01)
(52) U.S. Cl. .............................. 607/33; 607/2; 607/36; 607/9; 607/61; 128/903
(58) Field of Classification Search .................. 607/4, 607/5, 36, 33, 60, 61, 9, 34; 128/903; 600/302
See application file for complete search history.

(56) References Cited

U.S. PATENT DOCUMENTS

| | | | |
|---|---|---|---|
| 5,193,539 A * | 3/1993 | Schulman et al. ............ | 607/61 |
| 5,314,458 A * | 5/1994 | Najafi et al. ................. | 607/116 |
| 5,395,395 A * | 3/1995 | Hedberg ........................ | 607/7 |
| 5,814,089 A | 9/1998 | Stokes et al. | |
| 5,948,004 A * | 9/1999 | Weijand et al. ................ | 607/9 |
| 6,208,895 B1* | 3/2001 | Sullivan et al. ................ | 607/4 |
| 6,241,751 B1 | 6/2001 | Morgan et al. | |
| 6,266,567 B1 | 7/2001 | Ishikawa et al. | |
| 6,445,953 B1 | 9/2002 | Bulkes et al. | |
| 6,654,638 B1* | 11/2003 | Sweeney ........................ | 607/9 |
| 6,799,070 B2* | 9/2004 | Wolfe et al. ................... | 607/7 |
| 6,907,285 B2* | 6/2005 | Denker et al. ................. | 607/5 |

OTHER PUBLICATIONS

Digikey Corp. Catalog T051, 2005, pp. 969 & 974, for Panasonic Multilayer Ceramic Chip Capacitors.

* cited by examiner

*Primary Examiner*—Kennedy J. Schaetzle
(74) *Attorney, Agent, or Firm*—Quarles & Brady; George E. Haas

(57) ABSTRACT

An implantable device electrically stimulates an organ of an animal in response to a trigger event. Between trigger event that device receives a wireless signal, such as a radio frequency signal, and stores energy from the signal in a plurality of capacitors. The capacitors are located within a electrical lead that extends to a stimulation electrode attached to the organ. That electrical lead has a hollow outer insulating tube with a pair of conductors extending longitudinally therein. The plurality of capacitors are connected between the pair of conductors. Thus the electrical lead serves as both a conductor of a stimulation current to the electrode and a housing for the plurality of capacitors.

18 Claims, 2 Drawing Sheets

IMPLANTABLE MEDICAL STIMULATION APPARATUS WITH INTRA-CONDUCTOR CAPACITIVE ENERGY STORAGE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to implantable medical devices which produce electrical pulses that to stimulate organs of an animal, and more particularly to the storage of energy in such medical devices.

2. Description of the Related Art

A remedy for people with slowed or disrupted natural heart activity involves implanting a cardiac pacing device which is a small electronic apparatus that stimulates the heart to beat at regular rates.

Typically the pacing device is implanted in the patient's chest and has sensor electrodes that detect electrical impulses associated with in the heart contractions. These sensed impulses are analyzed to determine when abnormal cardiac activity occurs, in which event a pulse generator is triggered to produce electrical pulses. Wires carry these pulses to electrodes placed adjacent specific cardiac muscles, which when electrically stimulated contract the heart chambers. It is important that the stimulation electrodes be properly located to produce contraction of the heart chambers.

Modern cardiac pacing devices vary the stimulation to adapt the heart rate to the patient's level of activity, thereby mimicking the heart's natural action. The pulse generator modifies that rate by tracking the activity of the sinus node of the heart or by responding to other sensor signals that indicate body motion or respiration rate.

U.S. Pat. No. 6,445,953 describes a cardiac pacemaker that has a pacing device, which can be located outside the patient, to detect abnormal electrical cardiac activity. In that event, the pacing device emits a radio frequency signal, that is received by a stimulator implanted in a vein or artery of the patient's heart. Specifically, the radio frequency signal induces a voltage pulse in an antenna on the stimulator and that pulse is applied across a pair of electrodes, thereby stimulating adjacent muscles and contracting the heart.

Although this cardiac pacing apparatus offered several advantages over conventional pacemakers, it required that sufficient energy be derived from the received radio frequency signal to power the implanted circuit and to stimulate the adjacent organ. The amount of energy required may be relatively great, especially when the apparatus is an implantable defibrillator.

Therefore, it is desirable to provide an energy storage mechanism in the implanted apparatus which will accumulate energy from a radio frequency signal and provide that accumulated energy when needed for organ stimulation.

SUMMARY OF THE INVENTION

An apparatus is provided to artificially stimulate an organ of an animal. That apparatus includes a first electrode and a second electrode for implantation into the animal. An electrical lead has a first conductor and a second conductor with a plurality of capacitors connected to the first and second conductors. The plurality of capacitors may be connected in parallel or in series between the first and second conductors.

An element is provided for receiving wireless signals, which may be in the radio frequency spectrum, for example. A stimulation circuit is connected to the first electrode, the first conductor, the second conductor and the element. The stimulation circuit uses energy from a received first wireless signal to charge the plurality of capacitors with electrical energy. In response to a trigger event, the stimulation circuit applies the electrical energy from plurality of capacitors to the first and second electrodes to electrically stimulate the organ of the animal.

The trigger event may be the receipt of a second wireless signal that has a unique format which indicates that stimulation should occur. In this case, the second wireless signal may emanate from a pacing circuit that detects when artificial pacing of a heart if required. In another case, the wireless signal may emanate from a circuit that detects when cardiac defibrillation is required.

DETAILED DESCRIPTION OF THE INVENTION

Figure 1:
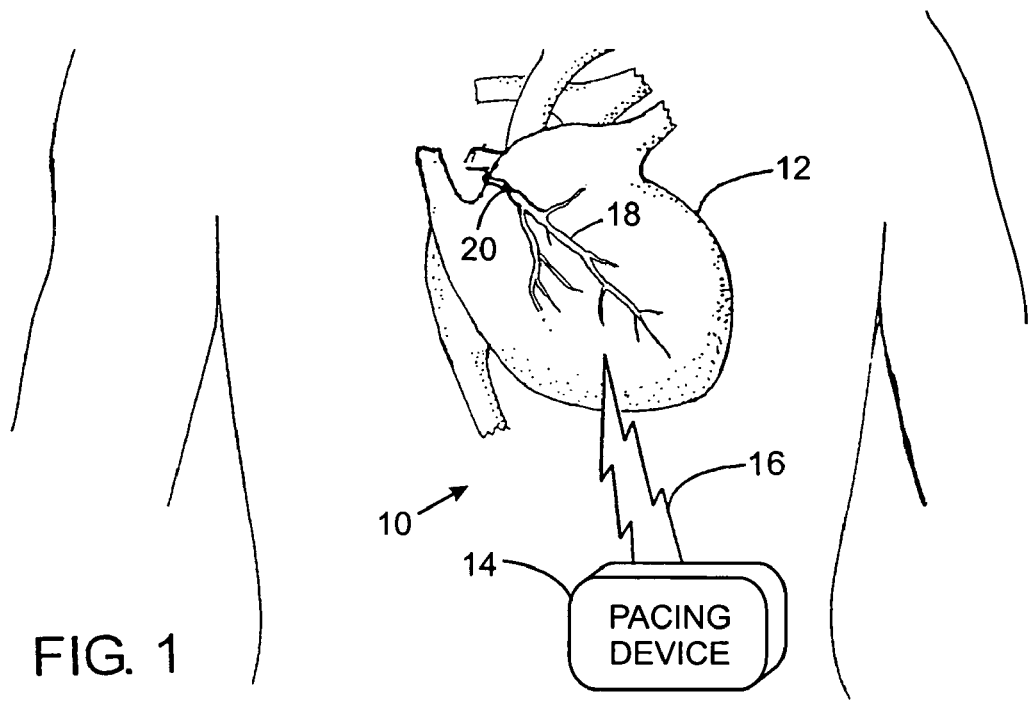
FIG. 1 is a representation of a cardiac pacing apparatus attached to a medical patient.

With initial reference to FIG. 1, a pacing apparatus 10 electrically stimulates a medical patient's heart 12 to contract or to convert from fibrillation to a normal rhythm. That apparatus comprises an external pacing device 14 and a stimulator 20 that is implanted in a blood vessel 18 of a muscle in the heart. As will be described in greater detail, the pacing device 14 transmits a radio frequency signal 16 which causes the stimulator 20 to emit an electric current that stimulates the heart muscle.

Figure 2:
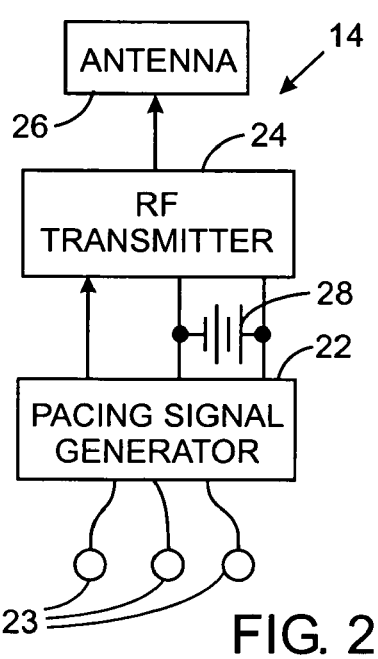
FIG. 2 is a circuit diagram of a power transmitter for the cardiac pacing apparatus.

Referring to FIG. 2, the pacing device 14, that preferably is worn outside the patient's body adjacent the chest, comprises a conventional pacing signal generator 22 connected to input electrodes 23 attached to the patient's body. Alternatively, the pacing device 14 may be implanted in the patient. The internal circuitry and operation of the pacing signal generator 22 are similar to prior cardiac pacers. However, instead of the output stimulation signals being applied to the electrodes via leads, the pacing signals are applied to an input of a radio frequency (RF) transmitter 24. In response to the stimulation signal (also known as a pacing signal) from the generator 22, the radio frequency transmitter 24 generates a pulse of the radio frequency signal 16 that is transmitted throughout the chest cavity via an antenna 26. Preferably the antenna 26 either is located relatively close to the heart 12 or is of a type which focuses the radio frequency signal toward the heart. Both the pacing signal generator 22 and the RF transmitter 24 are powered by a battery 28.

Figure 3:
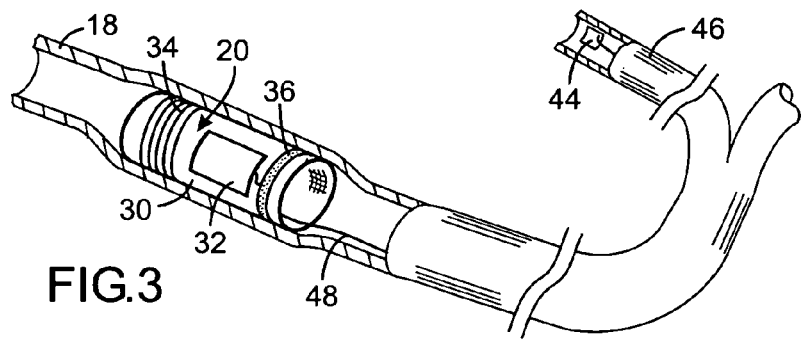
FIG. 3 is an isometric cut-away view of cardiac blood vessels in which a vascular stimulator and a second electrode have been implanted.

As illustrated in FIG. 3, the stimulator 20 is placed in an artery or vein 18 in close proximity to the atria or ventricles of the heart 12. For example the vascular stimulator 20 may be positioned in the coronary sinus vein. The stimulator 20 includes a body 30 similar to well-known expandable vascular stents that are employed to enlarge a restricted vein or artery. The body 30 has a generally tubular shape that initially is collapsed to a relatively small diameter enabling the stimulator to pass freely through blood vessels of a patient. The procedure for implanting the stimulator 20 is similar to that used for vascular stents. For example, a balloon at the end of a standard catheter is inserted into the stimulator 20 in a collapsed configuration. That assembly is inserted through an incision in a vein or artery near the skin of a patient and passed through the vascular system to the appropriate location proximate to the atria or ventricles of the heart 12. The balloon of the catheter then is inflated to expand the stimulator 20, thereby slightly enlarging the blood vessel 18 which embeds the stimulator in the wall of the vein or artery. The balloon is deflated, the catheter is removed from the patient, and the incision is closed. Alternatively, a self-expanding body 30 may be utilized. The slight enlargement of the blood vessel 18 and the tubular design of the body 30 allows blood to flow relatively unimpeded through the vascular stimulator 20.

Figure 4:
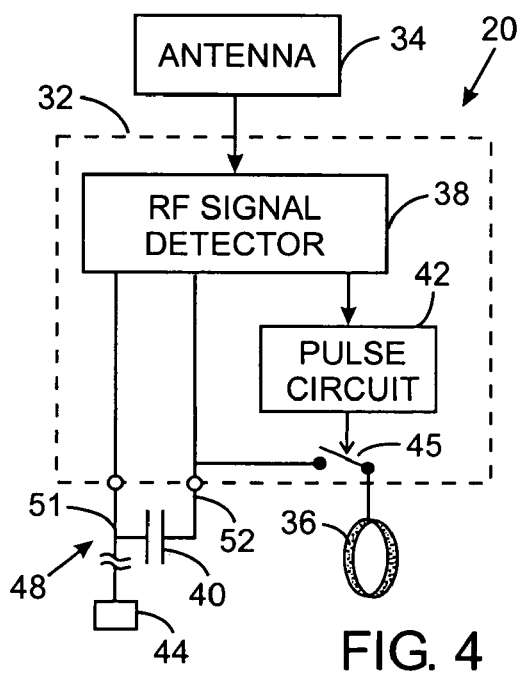
FIG. 4 is a block diagram of an electrical circuit on the vascular stimulator shown in FIG. 2.

With additional reference to FIG. 4, the stimulator 20 has a stimulation circuit 32 and a receive antenna 34 in the form of a wire coil wound circumferentially around the body 30. A first electrode 36 in the form of a ring encircles the body. The stimulation circuit 32 includes an RF signal detector 38 having an input connected to the receive antenna 34 and tuned to the frequency of the RF signal 16 that is emitted by the pacing device 14. The RF signal detector 38 converts the energy of that RF signal into an electric voltage that charges a storage capacitor 40 which supplies electrical power to the circuitry on the vascular stimulator 20. The periodic pulses of the RF signal charge the storage capacitor 40 so that it will have sufficient stored energy when stimulation of the heart is required.

A first electrode 36 in the form of a ring encircles the body is connected to one terminal of the storage capacitor 40. A second electrode 44 is adjacent to the wall of a blood vessel 46 in another section of the heart, as seen in FIG. 3, and is coupled to the stimulation circuit 32 by an insulated electrical lead 48 extending through the blood vessels. The relatively small size of the second electrode 44 allows it to be placed into a significantly smaller blood vessel 46 than the vascular stimulator 20. As a result, the second electrode 44 can be placed is a greater variety of locations in the cardiac vascular system and in close proximity to the muscles that contract the desired portion of the heart 12.

Figure 5:
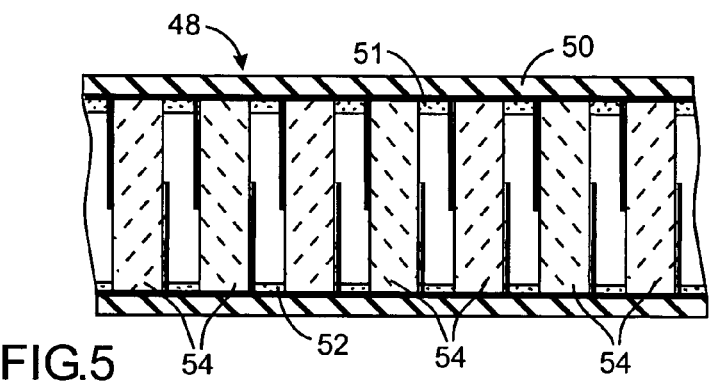
FIG. 5 is a longitudinal cross sectional view through an electrical conductor which contains energy storage capacitors according to the present invention.

In order to provide a enough electrical energy for stimulation, especially for defibrillation, as relatively large storage capacitance is required. Instead of placing that capacitance on the body 30 of the stimulator 20, a plurality of capacitors are placed along the length of the electrical lead 48 that connects the second electrode 44 to the stimulation circuit 32. With reference to FIG. 5, the electrical lead 48 has a tubular shell 50 of insulated material with two conductors 51 and 52 extending longitudinally along the central opening. A plurality of disk-shaped capacitors 54 also are spaced along that central opening. These capacitors 54 may be conventional surface mount type devices, such as model PCC2232CT which is 4.7 µf, 16 WVDC capacitor available from Panasonic Corporation of North America in Secaucus, N.J. 07094. The terminal on one side of each capacitor 54 is connected to the first electrical conductor 51 and the other terminal is connected to the second conductor 52. Therefore, the plurality of capacitors 54 are connected in parallel so that the individual capacitances are summed to form a large equivalent storage capacitor 40.

Figure 6:
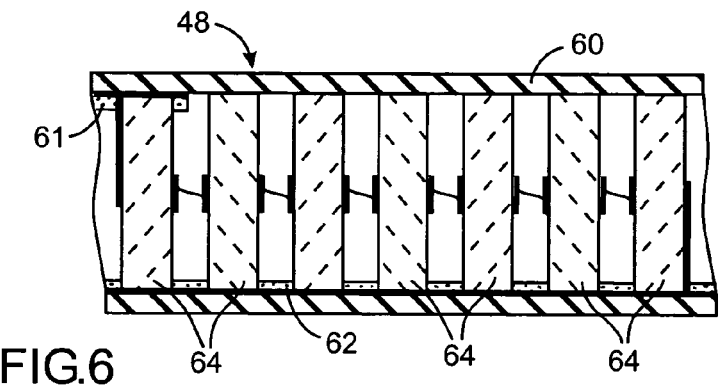
FIG. 6 is a longitudinal cross sectional view through a second electrical conductor which contains energy storage capacitors connected in series.

FIG. 6 illustrates an alternative structure for the electrical lead 48 which has an tubular insulated shell 60 with first and second conductors 61 and 62 extending longitudinally along the central opening. A plurality of disk-shaped capacitors 64 are connected in series between the first and second conductors 61 and 62, in contrast with electrical lead 48 in which the capacitors 54 are connected in parallel.

Referring again to FIG. 4, the pacing device 14 periodically transmits the radio frequency signal 16 to the stimulator 20. The RF signal detector 38 derives electrical voltage from the energy of that RF signal and applies that voltage across conductors 51 and 52 to charge the plurality of capacitors 64 that form the storage capacitor 40. Thus a sufficient charge is maintained on the storage capacitor 40 for when cardiac stimulation is needed.

The pacing device 14 also responds to the electrical signals from the heart, that are detected by the input electrodes 23, by determining in a conventional manner when cardiac stimulation is to required. When stimulation is to occur, the RF transmitter sends a uniquely shaped RF signal pulse sequence. The RF signal detector 38 in FIG. 4 responds to that RF signal pulse sequence by activating a pulse circuit 42 that closes a switch 45 connected to a second electrode. That action completes a circuit thereby dumping the voltage stored on the capacitor across the first and second electrodes 36 and 44 which stimulates the heart tissue between those electrodes.

Figure 7:
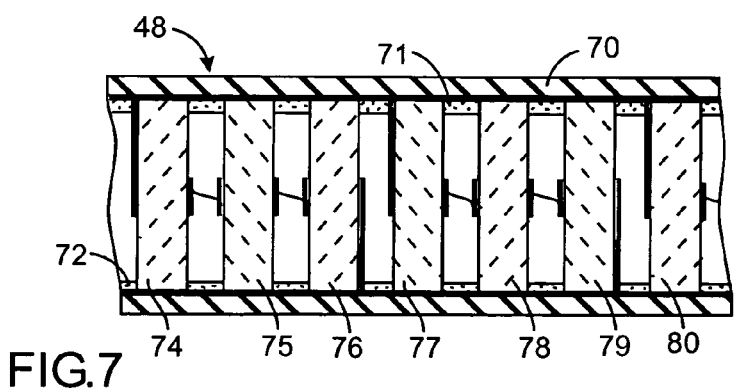
FIG. 7 is a longitudinal cross sectional view through another electrical conductor which contains energy storage capacitors connected in parallel in groups that are then connected in series.

FIG. 7 illustrates a third structure for the electrical lead 48 which has an tubular insulated shell 70 with first and second conductors 71 and 72 extending longitudinally along the central opening. A plurality of disk-shaped capacitors 74-80 are located within central opening. The capacitors are connected in groups with the devices in each group being coupled in series with the groups connected in parallel to the first and second conductors 71 and 72. Specifically, one group comprises capacitors 74, 75 and 76 that are connected in series with the first capacitor 74 in that group having a terminal that is coupled to the first conductor 71 and the last capacitor 76 in that group having a terminal that is coupled to the second conductor 72. Another group comprises capacitors 77, 78 and 79 connected in series with the first capacitor 74 coupled to the first conductor 71 and the last capacitor 76 coupled to the second conductor 72. The number of capacitors in each group and the number of groups are chosen to provide the desired cumulative capacitance and working voltage for the storage capacitor 40 of the stimulator 20.

The foregoing description was primarily directed to preferred embodiments of the invention. Even though some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

I claim:

1. An apparatus for artificially stimulating an organ of an animal, said apparatus comprising:
   a first electrode and a second electrode for implantation into the animal;
   an electrical lead having a shell containing a first conductor, a second conductor and a plurality of capacitors connected to the first and second conductors;
   a body for implantation in the animal, wherein the electrode lead extends from the body to a remote location in the animal;
   an element for receiving wireless signals; and
   a stimulation circuit connected to the first electrode, the first conductor, the second conductor and the element, the stimulation circuit using energy from a received first wireless signal to charge the plurality of capacitors with electrical energy, and responding to a trigger event by applying the electrical energy stored in the plurality of capacitors to the first electrode and the second electrode to electrically stimulate the organ of the animal.

2. The apparatus as recited in claim 1 wherein the plurality of capacitors connected in parallel between the first and second conductors.

3. The apparatus as recited in claim 1 wherein the plurality of capacitors connected in series between the first and second conductors.

4. The apparatus as recited in claim 1 wherein the plurality of capacitors are divided into groups with the capacitors in each group connected in series and the groups connected in parallel between the first and second conductors.

5. The apparatus as recited in claim 1 wherein the trigger event is a second wireless signal.

6. The apparatus as recited in claim 1 wherein the wireless signals are radio frequency signals.

7. The apparatus as recited in claim 6 wherein the first electrode is connected to the first conductor, and further comprising a switch coupling the second electrode to the second conductor, wherein the stimulation circuit responds to the trigger event by closing the switch.

8. The apparatus as recited in claim 1 wherein the stimulation circuit is mounted on the body, wherein the electrical lead extends from the body to the second electrode which is remote from the body.

9. The apparatus as recited in claim 1 wherein the first conductor of the electrical lead is attached to the second electrode.

10. The apparatus as recited in claim 1 wherein the stimulation circuit is mounted on the body, wherein the electrical lead extends from the body and has an end that is remote from the body.

11. An apparatus for implantation into an animal to artificially stimulate an internal organ, said apparatus comprising:
    a first electrode and a second electrode for implantation into the animal;
    an electrical lead having a shell, a first conductor, a second conductor and a plurality of capacitors connected to the first and second conductors;
    an antenna for receiving radio frequency signals;
    a body for implantation in the animal, wherein the electrical lead extends from the body to a remote location in the animal; and
    a stimulation circuit mounted to the body and connected to the first electrode, the first conductor, the second conductor and the antenna, the stimulation circuit using energy from a received first radio frequency signal to charge the plurality of capacitors with electrical energy, and responding to a trigger event by applying the electrical energy stored in the plurality of capacitors to the first electrode and the second electrode to electrically stimulate the organ of the animal.

12. The apparatus as recited in claim 11 wherein the plurality of capacitors connected in parallel between the first and second conductors.

13. The apparatus as recited in claim 8 wherein the plurality of capacitors connected in series between the first and second conductors.

14. The apparatus as recited in claim 11 wherein the plurality of capacitors are divided into groups with the capacitors in each group connected in series and the groups connected in parallel between the first and second conductors.

15. The apparatus as recited in claim 11 wherein the trigger event is a second radio frequency signal.

16. The apparatus as recited in claim 11 wherein further comprising a switch coupling the first electrode to the second conductor, wherein the stimulation circuit responds to the trigger event by closing the switch.

17. The apparatus as recited in claim 11 wherein the electrical lead extends from the body to the second electrode which is remote from the body.

18. The apparatus as recited in claim 11 wherein the first conductor of the electrical lead is attached to the second electrode.

* * * * *

UNITED STATES PATENT AND TRADEMARK OFFICE
CERTIFICATE OF CORRECTION

PATENT NO. : 7,310,556 B2 Page 1 of 1
APPLICATION NO. : 11/089476
DATED : December 18, 2007
INVENTOR(S) : Cherik Bulkes It is certified that error appears in the above-identified patent and that said Letters Patent is hereby corrected as shown below:

Column 6, Line 30, claim #13:
"in claim 8" should be --in claim 11--

Signed and Sealed this

Twenty-ninth Day of April, 2008

JON W. DUDAS
*Director of the United States Patent and Trademark Office*